United States Patent [19]

Davis

[11] Patent Number: 5,290,705
[45] Date of Patent: Mar. 1, 1994

[54] SPECIMEN SUPPORT FOR OPTICAL ANALYSIS

[75] Inventor: Robert E. Davis, Hinsdale, Ill.

[73] Assignee: R. E. Davis Chemical Corporation, Oak Brook, Ill.

[21] Appl. No.: 820,302

[22] Filed: Jan. 13, 1992

[51] Int. Cl.$^5$ .............................................. G01N 21/00
[52] U.S. Cl. ...................................... 436/164; 422/99; 422/102; 422/104; 356/244; 356/246
[58] Field of Search ................. 422/57, 102, 99, 104; 356/244, 323, 246; 436/164; 446/15, 21; D21/61

[56] References Cited

U.S. PATENT DOCUMENTS

| | | |
|---|---|---|
| 3,873,268 | 3/1975 | McKie, Jr. ............................ 422/102 |
| 4,305,663 | 12/1981 | Perkins et al. ........................ 356/323 |
| 4,682,890 | 7/1987 | de Hacario et al. ................... 356/246 |
| 4,844,866 | 7/1989 | Wallace et al. ........................ 422/57 |
| 5,006,474 | 4/1991 | Horstman et al. ..................... 422/58 |
| 5,074,662 | 12/1991 | Sullivan ................................. 422/102 |

Primary Examiner—James C. Housel
Assistant Examiner—Lien Tran
Attorney, Agent, or Firm—Andrus, Sceales, Starke & Sawall

[57] ABSTRACT

A specimen support for optical observation or analysis. The support comprises a disc-like member composed of a rigid material and having at least one unobstructed hole extending therethrough. When analyzing a liquid specimen, the disc is dipped in the liquid and the surface tension of the liquid will cause the liquid to bridge or span the hole. The support is then placed in a tray or holder and exposed to an infrared beam to generate an infrared spectrum.

6 Claims, 1 Drawing Sheet

SPECIMAN SUPPORT FOR OPTICAL ANALYSIS

BACKGROUND OF THE INVENTION

Infrared microspectroscopy can be used to provide an infrared spectrum of liquid and solid materials. In a typical apparatus of this type a source of infrared energy is directed through the specimen which is supported on an optically clear disc-like window, and mirrors are employed to vary the wavenumber or length of the beam and generate an infrared spectrum of a specific area of the specimen. The window used in an apparatus of this type is generally composed of a crystal such as KBr, BaF$_2$, or the like, which is capable of transmitting infrared radiation.

When analyzing a solid specimen, such as animal or plant tissue, paint flakes, or the like, a thin section of the specimen, generally having a thickness in the range of 5 to 15 microns, is mounted on the window. It is important that the specimen have a thickness in the above-mentioned range, for if the specimen is too thick, distorted spectra are obtained, in which strong bands flatten out and weak bands are disproportioned. It is also important to hold the specimen flat against the window, and this is generally accomplished by either clamping the specimen between two windows or discs, or holding the specimen taut against a surface of the window through use of tape or the like.

When analyzing a liquid specimen, a thin film of the liquid is applied to the surface of the disc-like window. However, the conventional windows, as used in the past will not tolerate water or acidic materials, for the water or acidic materials will attack the window, which will cause loss of specimen integrity. The procedure, as used in the past, for analyzing aqueous solutions, has been to initially distill off the water to obtain a solid or viscous liquid and then neutralize the residue. The residue is then extracted with a solvent which will not attack the window. The solvent solution is then placed on a surface of the window and an infrared spectrum can them be obtained. However, the spectrum of the solvent itself, as well as the spectrum of the window, must be deducted from the composite spectrum. It has also been noted that when using this extraction method, there is some loss of specimen integrity, due to the processing involved.

As a further problem, the disc-like windows, as used in the past to support the specimens,,are very expensive and in most cases are discarded after use, or alternately, require costly surface repolishing before re-use.

SUMMARY OF THE INVENTION

The invention is directed to a specimen support for observation or analysis and in particular to a specimen support that can be used in infrared microspectroscopy. The support of the invention comprises a disc-like member which is composed of a rigid material, such as plastic or metal, and has at least one hole, and preferably a plurality of holes, extending therethrough. The holes each have a cross-sectional area that is correlated to the surface tension of a liquid specimen to be analyzed, so that when the support is dipped in the liquid, the liquid, by virtue of its surface tension, will span or bridge the hole. In general, the holes have a diameter, or average cross sectional dimension, in the range of about 10 microns to 13 millimeters.

After dipping, the disc is installed in a holder or tray and placed in the microspectroscopy apparatus, where an infrared beam is directed through the unsupported liquid film which spans the hole, to thereby generate an infrared spectrum.

When analyzing a sold specimen, such as fibers, paint flakes, or the like, the specimen is held against a surface of the disc, spanning the hole, or alternately, the specimen is inserted and clamped within the hole.

As the support or disc of the invention is formed of a material which will not be attacked by either water or acids, aqueous and acidic solutions can be directly analyzed which eliminates the time consuming and costly extraction processes that were required in the past to extract the dissolved components into a solvent which would be compatible with the specimen-supporting windows.

The specimen supports or discs of, the invention, when formed of a material such as a thermoplastic resin or stainless steel, are relatively inexpensive as compared to the optically clear crystal windows, as used in past procedures.

By incorporating holes of different diameter in the support, hole-bridging films of a liquid specimen of different thicknesses can be obtained, so that the operator can then select the desired film thickness to provide a good quality spectrum.

The crystal windows, as used as specimen supports in the past, are each capable of transmitting only a given range of wavelength and wavelengths outside of that range are absorbed. On the other hand, with the invention, the specimen to be analyzed is not mounted on an infrared transmitting support, but instead is unsupported in the hole in the support disc, with the result that the wavelength band is restricted only by the detector.

Other objects and advantages will appear in the course of the following description.

DESCRIPTION OF THE DRAWINGS

The drawings illustrate the best mode presently contemplated of carrying out the invention.

In the drawings.

DESCRIPTION OF THE ILLUSTRATED EMBODIMENT

Figure 1:
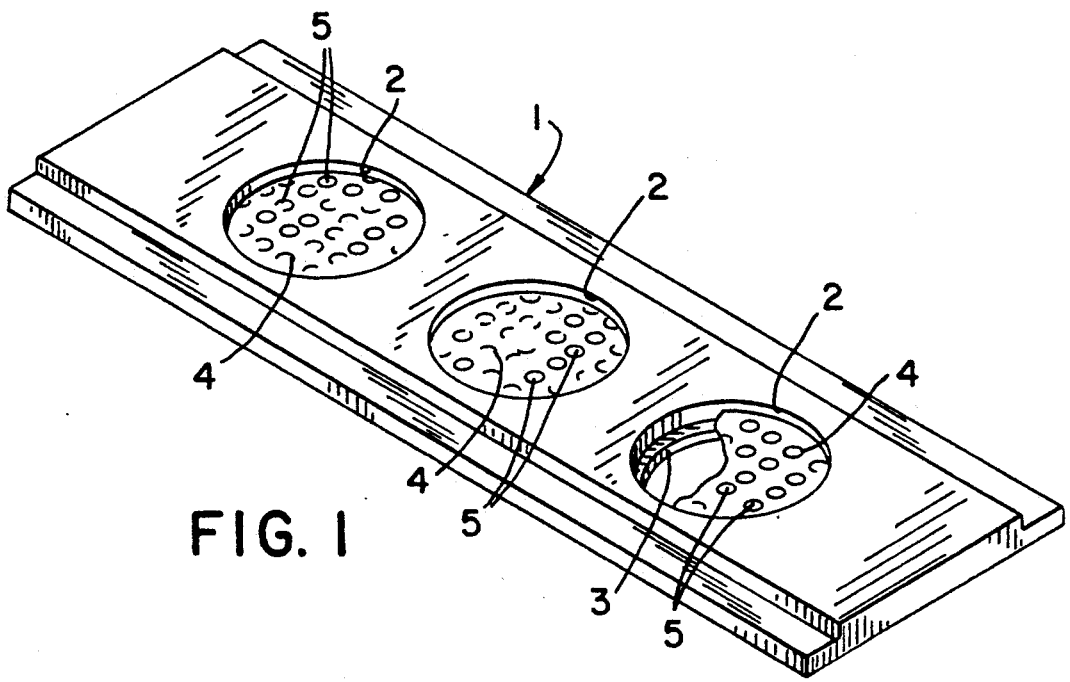
FIG. 1 is a perspective view of a holder containing the specimen supports of the invention.

The drawings show a specimen tray or holder 1 to be employed for optical observation or analysis and has particular application for use in infrared microspectroscopy. The holder 1 includes one or more openings and each opening is provided with an internal ledge or shoulder 3 and a specimen support 4 of the invention is supported on each ledge 3. Each support 4 is preferably a disc-like member having a pair of generally flat, parallel, opposed surfaces and one or more unobstructed holes 5 extend through the support between the opposed surfaces.

Each support 4 is formed of a generally rigid material which will not be attacked by water or acids. Metals, such as stainless steel or gold; or plastic materials such as nylon, polytetrafluoroethylene (Teflon), or Kevlar, can be used to produce the support 4.

As shown in the drawings, holes 5 are generally circular in cross section, but it is contemplated that the holes can have other cross-sectional configurations. Holes 5 have a diameter greater than 10 microns, generally in the range of about 10 microns to 13 millimeters. The cross sectional area or diameter of the holes is correlated with the surface tension of a liquid specimen to be analyzed, such that a film 6 of the liquid will span or enclose the holes, as shown in FIG. 2.

Figure 2:
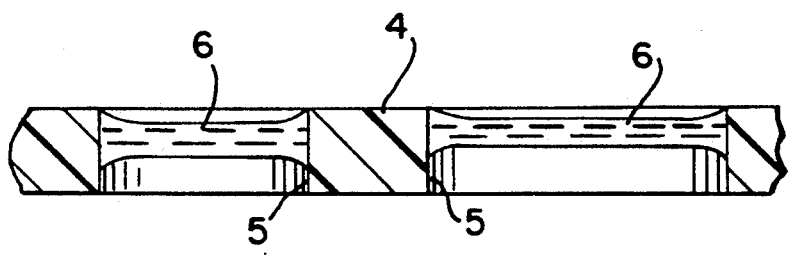
FIG. 2 is a diagrammatic cross section of a support showing films of a liquid specimen bridging the holes in the support.

Holes 5 can all be of the same diameter or cross-sectional area, or alternately as illustrated in FIG. 2, the holes can have different diameters. With different diameter holes, the thickness of the liquid film 6 which bridges or encloses the holes will vary with the hole diameter, and thus the operator can select a film thickness to provide the best quality spectrum.

As shown in FIG. 2, the liquid film 6 which bridges the holes 5 should be relatively thin and free of "lensing". In general, the film 6 will have a thickness to provide a spectrum when the infrared beam is passed through the film, while the maximum thickness will be less than that necessary to produce a "lensing" effect. "Lensing" is a condition in which a surface of the film is convex or dome-like, which will prevent good quality readings from being obtained.

When analyzing a liquid specimen containing dissolved constituents, the liquid can be conveniently applied to the holes 5 by dipping the support 4 in the liquid. As previously noted, the diameter of the holes 5 is correlated with the surface tension of the liquid, so that the liquid will bridge or enclose the holes. The support 4 is then mounted in the holder 1 and installed in the microspectroscopy apparatus. By directing an infrared beam through the unsupported film in one of the selected holes, an infrared spectrum of the specimen can be generated.

When analyzing a solid specimen, the specimen can be changed on a surface of the support 4, spanning a hole 5, or alternately, as in the case of a fiber, the solid specimen can be inserted and clamped in hole 5.

As the support 4 is formed of a material which will not be attacked by either water or acidic components, aqueous or acidic liquid specimens can be directly analyzed without the need of extracting in a solvent solution, as used in the past.

As the specimen to be analyzed is located within the unobstructed hole in the support and is not supported on a light transmitting window, it is not necessary to deduct the spectrum of a light-transmitting window from the generated spectrum. Further, a light transmitting window may contain fingerprints, scratches, or other surface defects which could adversely affect the integrity of the generated spectrum.

By employing holes 5 of different diameter in a single support 4, different thicknesses of a liquid film 6 can be obtained, so that the operator can select the desired film thickness to provide the best quality spectrum.

Various modes of carrying out the invention are contemplated as being within the scope of the following claims particularly pointing out and distinctly claiming the subject matter which is regarded as the invention.

We claim:

1. A method of analyzing a liquid specimen, comprising the steps of forming a specimen support of a rigid material that is non-reactive to water and acidic substances and having a pair of opposed surfaces and having a plurality of unobstructed holes extending between said surfaces, a first of said holes having a different cross sectional area than a second of said holes, positioning said support so that said surfaces are horizontal and the axes of the holes are vertical, enclosing each hole with an unsupported film of a liquid specimen to be analyzed, directed a beam of infrared light through the hole and through the liquid film enclosing the hole, and generating a wavelength spectrum of said beam passing through said film.

2. The method of claim 1, wherein the step of enclosing the holes comprises dipping the support in a quantity of said liquid specimen.

3. The method of claim 1, and including the step of forming the film of each liquid specimen with a thickness sufficient to provide a spectrum when said beam is passed through said film, said film having a pair of generally parallel surfaces substantially free of convexity that extend transversely across said holes.

4. The method of claim 1, and including the step of maintaining the thickness of said film at a value less than that necessary to cause lensing.

5. An analytic specimen support for infrared microspectroscopy, comprising a holder having a confined opening extending therethrough, support means provided in the opening, and a specimen support removably disposed in the opening and mounted on said support means, said specimen support composed of a rigid material that is non-reactive to water, acidic substances and solvents, said specimen support including a pair of opposed generally flat horizontal surfaces and having a plurality of unobstructed holes extending between said surfaces with the axes of the holes being vertical, a film of a liquid specimen spanning each hole and held in said hole by the surface tension of the liquid, the film spanning each of said holes having generally parallel opposed surfaces and being free of convexity, a first of said holes having a different cross sectional area than a second of said holes.

6. The support of claim 5, wherein said holes have a diameter in the range of 10 microns to 13 millimeters.

* * * * *